United States Patent [19]
Saifer et al.

[11] Patent Number: 5,080,891
[45] Date of Patent: Jan. 14, 1992

[54] CONJUGATES OF SUPEROXIDE DISMUTASE COUPLED TO HIGH MOLECULAR WEIGHT POLYALKYLENE GLYCOLS

[75] Inventors: Mark Saifer, Berkeley; Ralph Somack, Oakland; L. David Williams, Fremont, all of Calif.

[73] Assignee: DDI Pharmaceuticals, Inc., Mountain View, Calif.

[21] Appl. No.: 560,996

[22] Filed: Aug. 1, 1990

Related U.S. Application Data

[63] Continuation of Ser. No. 380,205, Jul. 13, 1989, Pat. No. 5,006,333, which is a continuation-in-part of Ser. No. 81,009, Aug. 3, 1987, abandoned.

[51] Int. Cl.$^5$ .................... A61K 31/74; A61K 37/48
[52] U.S. Cl. .................... 424/78.3; 424/94.1; 435/180; 435/181
[58] Field of Search ............. 424/78, 94.1; 435/180, 435/181

[56] References Cited

U.S. PATENT DOCUMENTS

| | | | |
|---|---|---|---|
| 4,179,337 | 12/1979 | Davis et al. | 424/78 |
| 4,563,349 | 1/1986 | Miyato et al. | 435/189 |

FOREIGN PATENT DOCUMENTS 0200467  4/1986  European Pat. Off.

OTHER PUBLICATIONS

Enrico Boccu et al., "Coupling of Monomethoxypolyethyleneglycols to Proteins via Active Esters", Z. Naturforsch, 38c, pp. 94-99 (1983).
Enrico Boccu et al., "Pharmacokinetic Properties of Polythylene Glygol Derivated Superoxide Dismutase", Pharmacological Research Communications, vol. 14, pp. 113-120 (No. 2) (1982).
Weng Y. Lee et al., "Suppression of Reaginic Antibodies with Modified Allergens", Int. Archs. Allergy Appl. Immun., vol. 56, pp. 159-170 (1978).
Weng Y. Lee et al., "Suppression of Reaginic Antibodies with Modified Allergens", Int. Archs. Allergy Appl. Immun., vol. 56, pp. 193-206 (1978).
Weng Y. Lee et al., "Suppression of Reaginic Antibodies with Modified Allergens", Int. Archs. Allergy Appl. Immun., vol. 64, pp. 100-114 (1981).
U. Mueller et al., "Studies of Chemically Modified Honeybee Venom", Int. Archs. Allergy Appl. Immun., vol. 68, pp. 312-319 (1982).
U. Mueller et al., "Studies of Chemically Modified Honeybee Venom", Int. Archs. Allergy Appl. Immun., vol. 68, pp. 320-325 (1982).
Peter S. Pyatak et al., "Preparation of a Polyethylene Glycol: Superoxide Dismutase Adduct, and an Examination of its Blood Circulating Life and Anti-Inflammatory Activity", Res. Commun. Chem. Pathol. Pharmacol., vol. 29, No. 1, pp. 113-127 (1980).
F. M. Veronese et al., "Surface Modification of Proteins", Appl. Biochem. Biotech., vol. 11, pp. 141-152 (1985).
S. I. Wie et al., "Suppression of Reaginic Antibodies with Modified Allergens", Int. Archs. Allergy Appl. Immun., vol. 64, pp. 84-99 (1981).
Takayuki Yoshimoto et al., "Characterization of Polyethylene Glycol-Modified L-Asparaginase from Escherichia Coli and Its Application to Therapy of Leukemia", Jpn. J. Cancer Res. (Gann), vol. 77, pp. 1264-1270 (Dec. 1986).
G. E. C. Sims et al., "A Method for the Estimation of Polyethylene Glycol in Plasma Protein Fractions", Anal. Biochem., vol. 107, pp. 60-63 (1980).
C. A. Beauchamp et al., "A New Procedure for the Syntheis of Polyethylene Glycol-Protein Adducts; Effects on Function, Receptor Recognition, and Clearance of Superoxide Dimutase, Lactoferrin, and 2-Macroglobulin", Analytical Biochemistry, vol. 131, No. 1, May 1983, Academic Press, New York, pp. 25-33.
"Polyethers (Ethylene Oxide Polymers)", Kirk-Othmer Encyclopedia of Chemical Technology, vol. 18, 3rd Ed., John Wiley & Sons, Publ., pp. 616-632, Aug. 10, 1982.

*Primary Examiner*—Thurman K. Page
*Assistant Examiner*—Peter F. Kulkosky
*Attorney, Agent, or Firm*—Wegner, Cantor, Mueller & Player

[57] ABSTRACT

A biologically persistent, water-soluble, substantially non-immunogenic, substantially non-antigenic conjugate of superoxide dismutase is prepared by coupling one to five strands of a polyalkylene glycol which is polyethylene glycol or polyethylene-polypropylene glycol copolymer, wherein said polyalkylene glycol has an average molecular weight of about 35,000–1,000,000.

10 Claims, No Drawings

CONJUGATES OF SUPEROXIDE DISMUTASE COUPLED TO HIGH MOLECULAR WEIGHT POLYALKYLENE GLYCOLS

This application is a continuation of Ser. No. 07/380,205, filed July 13, 1989, now U.S. Pat. No. 5,006,333, which is a continuation-in-part application of parent application Ser. No. 081,009 filed Aug. 3, 1987 now abandoned.

The present invention is directed to superoxide dismutase (SOD) conjugates or adducts in which at least a portion of the SOD amino, carboxyl, or sulfhydryl groups are coupled to a polyalkylene glycol (PAG), such as a polyethylene glycol (PEG) or a polyethylene-polypropylene glycol copolymer, wherein the PAG has a molecular weight greater than 20,000 and desirably an average molecular weight of about 35,000 to 1,000,000 daltons. Unless otherwise indicated, molecular weights for PAG are those determined by high performance, size exclusion liquid chromatography (HPLC) using PEG as standard. Preferred is a PAG with an average molecular weight of about 40,000 or greater but no greater than 200,000 and especially preferred is an average molecular weight for the PAG of about 40,000–150,000. Such PAG can be linear or branched and be unsubstituted or substituted by straight-chained or branched $C_{1-4}$-alkyl groups to form a $C_{1-4}$-alkoxy group. Of special value to prevent linkage to two SOD molecules are PAG molecules in which one terminal group is a $C_{1-4}$-alkyl ether group such as an isopropoxy group. PAG, which is a mixture of terminally-substituted and unsubstituted molecules (e.g., partially isopropylated), can also be used.

BACKGROUND OF THE INVENTION

Previous workers have utilized PEG or methoxy-PEG of low molecular weight (350 to 20,000, and typically about 5,000) attached to superoxide dismutase (SOD) and other proteins to obtain adducts demonstrating varying degrees of (a) increased serum persistence and (b) reduced immunogenicity. However, the extent of modification of protein groups with low molecular weight PEG or methoxy-PEG required to adequately attain both objectives (a) as well as (b), often leads to substantial losses in enzyme activity or biological activity. For example, Pyatak et al. (Res. Commun. Chem. Pathol. Pharmacol. 29, 113–127, 1980) showed that attaching 7 to 18 methoxy-PEG strands (MW 5000, each strand) to SOD produced adducts demonstrating a serum half life of about 25 hours in mice but which retained only 50%–60% of the native enzyme activity. Attaching fewer PEG strands of MW 5000 gave adducts of higher enzyme activity but reduced the serum persistence (to about 10 hours.)

Yoshimoto et al. (Jpn. J. Cancer Res. 77, 1264–1270, 1986) have attempted to solve the reduced activity problem observed with L-asparaginase, by modifying fewer protein groups using a chloro-triazine reagent substituted with two strands of methoxy-PEG, each strand having a molecular weight in the same range (5000 or less) employed by others. However, cyanuric chloride is toxic to animals and many workers have cautioned against introducing a triazine ring into an adduct used for pharmaceutical purposes, since this chemical moiety would be anticipated to be immunogenic. Yabuki and Iwashita (European Patent Application #86303058.1, filed Apr. 23, 1986) substituted PEG for methoxy-PEG, but in the same MW range employed by other workers, to prepare adducts which claim to be composed of SOD copolymers in which both ends of the PEG are attached to different SOD molecules. They report serum half-lives for these adducts of 4 to 8 hours. Other workers, including Lee and Sehon (Int. Archs. Allergy Appl. Immun., 56, 159–170, 1978), Lee and Sehon (ibid., 56, 193–206, 1978) and Mueller et al., (ibid., 68, 312–319, 1982 and ibid., 68, 320–325, 1982) had previously used PEG in the same MW range (6,000–20,000) as Yabuki and Iwashita to produce adducts which probably contained similar copolymer structures. Wie et al. (Int. Archs. Allergy Appl. Immun., 64, 84–99, 1981) and Lee et al. (ibid., 64, 100–114, 1981) specifically replaced PEG with methoxy-PEG in the 2000–20,000 MW range to avoid possible inter- and intramolecular linkages.

DETAILS OF THE INVENTION

Superoxide dismutase (SOD) is an intracellular enzyme responsible for catalyzing the conversion of the superoxide radical to oxygen and hydrogen peroxide. Native orgotein protein has been shown to possess uniquely high SOD activity. Amongst the fields of application studied for orgotein have been inflammatory conditions such as arthritis and related conditions, cystitis, epicondylitis, tendovaginitis, bursitis, uses in cardiology including reperfusion injury following ischemia associated with myocardial infarction, congestive failure, arteriosclerotic cardiovascular disease, pulmonary conditions, oxygen toxicity, reperfusion injury following ischemia associated with organ transplantation, immune complex disease, dermatological conditions and in avoiding side-effects of radiotherapy. Preferred methods of administration include injection into joint spaces or musculoskeletal junctions. Such administration is commonly preferred to delay systemic inactivation, which occurs especially in the kidneys.

It is an object of the invention to provide a product which is more persistent than the native SOD protein in vivo and to delay inactivation by the kidneys. It is especially important that the product retain enzymatic activity for a prolonged time while exhibiting a low level of immunogenicity.

It is also a special object of this invention to provide a conjugate with anti-inflammatory activity, as shown, e.g., in the conventional carrageenan-induced paw edema test. This activity makes the product especially promising for treatment of rheumatoid conditions.

The novel concept embodied in the present invention utilizes high molecular weight PAG strands, greater than 20,000. The PAG used in the present invention can be any water soluble polymer of alkylene oxide, for example, poly(ethylene oxide) or certain copolymers of ethylene oxide and propylene oxide. The PAG can be linear or branched and can be substituted at one or more hydroxyl positions (but not at all terminal hydroxy groups) with a $C_{1-4}$-alkyl group or other chemical group. However, the molecular weight of the PAG polymer used for the preparation of the conjugate in the present invention is greater than 20,000 and preferably in the 35,000 to 200,000 MW range and especially about 40,000 to 150,000. Use of polymers larger than 200,000 is also possible but they are not preferred due to their higher viscosity and susceptibility to cleavage by shearing.

The PAG-SOD adducts of the present invention have molecular weights (relative to PEG standards of known molecular weight) ranging from about 40,000 to about 2,000,000 daltons, and preferably about 90,000 to 1,000,000 daltons. Furthermore, the PAG-SOD adducts of the present invention usually retain most of the enzymatic activity of the native protein. (It is to be noted that molecular weights herein are based on PEG standards of known molecular weight. For the purpose of HPLC calibration, the protein equivalent molecular weights, i.e., MW based on protein standards of known MW, appear to be approximately 5 to 8 times larger).

The conjugates of the present invention are an improvement over previous products in that by attaching fewer PAG strands, less chemical modification of the active parent molecule results, so that more of the original character of the parent molecule is preserved. Thus, by using fewer strands of high molecular weight PAG, as in the present invention, the adducts retain most, if not substantially all of the activity of the parent molecule, while also demonstrating increased persistence in the bloodstream. Another advantage of the adducts of the present invention is that by using high molecular weight PAG, larger adducts can be made with the same degree of modification attained by other workers. Furthermore, in some applications, larger PAG adducts are clearly advantageous. For example, PEG-SOD adducts of this invention, which were prepared using PEG-strands in the 40,000-130,000 MW range by the methods of this invention and which illustrate the principle of this invention, had serum half-lives in mice of about 36 hours and greater, longer than the PEG-SOD adducts described by previous workers.

The PAG-SOD adducts preferably contain from 1 to 5 chains of attached PAG per protein molecule, and more preferably 2 to 4 chains of PAG per molecule. The number of chains needed to achieve satisfactory serum persistence decreases when longer chains are used.

The SOD preparations of this invention are typically the mammalian copper- and zinc-containing superoxide dismutase forms of the enzyme derived from bovine, other animal (e.g., sheep, horse, pig, dog, rabbit, chicken) or human cells. Also available are SOD preparations containing other metal ions such as iron or manganese. Also useful is the enzyme with congeneric structures derived from microbial cultures in which such structures have been cloned and expressed. The SOD may also be non-identical to the naturally occurring proteins as a result of infidelity of translation in such microbial cultures, since the products of this invention have reduced immunogenicity.

It has also been found that when the SOD preparation contains traces of non-SOD proteins which would otherwise make such preparation immunologically unsafe for repeated parenteral administration, coupling such SOD by the methods of this invention can render the product reasonably useful, since the impurity proteins are rendered substantially less immunogenic.

In the coupling process, a number of conventional reactions can be used.

A preferred reaction proceeds by way of formation of a reactive carbonate half ester, PAG-O-CO-X, wherein X is a good leaving group, using reagents such as carbonyl diimidazole, p-nitrophenyl chloroformate or bis-N-succinimidyl carbonate. The activated PAG, PAG-O-CO-X, is then reacted with the protein under conditions which do not destroy its enzymatic activity, leading predominantly to urethane linkages

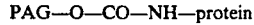

PAG—O—CO—NH—protein attached through protein amino groups such as the epsilon-NH$_2$ group of lysine.

For example, carbonyl diimidazole, can be reacted with the terminal hydroxyl groups of the PAG. The reaction mixture is quenched in aqueous solution at neutral pH and the activated PAG (polyalkylene glycol-carbonyl-imidazole) is isolated by dialysis and/or size exclusion chromatography.

Reaction of the

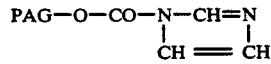

with SOD is carried out in solution, with an excess of activated PAG.

In a variant of this reaction, a solution of SOD and activated PAG is freeze-dried. The coupled products are conveniently isolated by size exclusion chromatography. Other purification processes can be employed including ion exchange chromatography.

In an alternate coupling reaction, the polyalkylene glycol is dissolved in an inert organic solvent, the reaction mixture is rendered weakly alkaline and reacted with cyanuric chloride.

The unreacted cyanuric chloride is removed by precipitating the PAG with petroleum ether. The residual solvent is evaporated to yield a 2-PAG-6-chloro-1,3,5-triazine. The resulting activated polymers are then reacted with SOD in a suitable buffer, e.g., a borate solution. The unreacted activated PAG is removed and the product isolated by chromatography. There is thus obtained a 4-hydroxy-1,3,5-triazine to which there is attached at the 2-position the polyalkylene glycol group PAG—O— while at the 6-position there is attachment to the epsilon-amino group of a reactive lysine group of SOD.

A terminal hydroxy group of PAG can also be converted to a carboxyl group, e.g., by reaction with succinic anhydride or with ethyl bromoacetate and alkali, or by oxidation of the terminal —OCH$_2$CH$_2$OH with alkaline permanganate to form the PAG acetic acid ethers, PAG—O—CH$_2$—COOH. The carboxyl groups are then activated by methods commonly known to be useful for protein modification, e.g., formation of the N-hydroxy succinimide ester by reaction with a carbodiimide and N-hydroxysuccinimide, or formation of the acyl azide by nitrosation of the acyl hydrazide. The activated PAG is then reacted with the protein under conditions which do not destroy the enzymatic activity of the protein, leading predominantly to amide linkages (PAG—C(=O)NH—protein) via protein amino groups (such as amino terminal NH$_2$ and lysine epsilon amino groups).

A terminal PAG hydroxyl group can also be converted to an amino group, e.g., by reaction first with thionyl bromide to form PAG—Br, followed by aminolysis with excess ammonia to form PAG—NH$_2$. The amino-PAG can then be coupled through amide bonds directly to the protein carboxyl groups by use of reagents such as water-soluble carbodiimide or Woodward's Reagent K. Alternatively, the amino function can be converted to a carboxylic acid function, e.g., by reaction with succinic anhydride, which is then activated and reacted with the protein in the manner described above.

The PAG terminal —CH$_2$OH can also be converted to an aldehyde group, —CH(=O) e.g., by oxidation with MnO$_2$. The aldehyde group can then be reductively alkylated onto the protein via the latter's free amino groups, e.g., with cyanoborohydride, to give a linkage predominantly via secondary amine groups, forming a PAG—OCH$_2$CH$_2$NH-protein bridge.

In addition to protein amino groups, protein carboxyl and sulfhydryl groups can also be used for coupling to the PAG.

As stated above, in selecting coupling reactions, those are preferred which leave only non-aromatic groups composed of carbon, oxygen, sulfur, nitrogen and hydrogen as part of the bridge linking the PAG to the protein.

The conjugated SOD can be isolated from the reaction solution, preferably after dialysis to remove extraneous ions, by conventional lyophilization. If desired or necessary, the conjugate can be further purified by ion exchange chromatography, electrophoresis, and/or gel filtration.

Filtration through a micropore filter in a conventional manner into sterile vials, optionally after adjusting ionic strength, e.g., with sodium chloride and/or sodium phosphate to isotonicity, provides a sterile solution suitable for administration by injection.

The pharmaceutical compositions of this invention comprise PAG-SOD conjugates of this invention and a pharmaceutically acceptable carrier.

The pharmaceutical composition preferably is in the form of a sterile injection preparation, for example a sterile injectable aqueous solution. The solution can be formulated according to the known art using pharmaceutically acceptable carriers mentioned above. The sterile injectable preparation can also be a solution or suspension in a non-toxic parenterally acceptable diluent or solvent.

The compositions of this invention combine an effective unit dosage amount of SOD conjugate at a concentration effective to evoke the desired response when a unit dose of the compositions is administered by the route appropriate for the particular pharmaceutical carrier. For example, liquid compositions usually contain about 0.5 to 40 mg of conjugate protein per 0.25 to 10 ml, preferably about 0.5 to 5 ml, except I.V. infusion solutions, which can also be more dilute, e.g., 0.5 to 200 mg SOD conjugate protein per 50–1,000 ml, preferably 100–500 ml, of infusion solution. Tablets, capsules and suppositories usually contain 0.1 to 25 mg, preferably 1 to 10 mg, of conjugate protein per dosage unit.

The SOD conjugates of this invention, like the established product orgotein, are effective in treating a wide variety of inflammatory conditions, including those in which synthetic anti-inflammatory agents have limited utility, e.g., because of toxic side effects upon prolonged use.

More specifically, the SOD conjugates are efficacious in ameliorating damage to the lungs from oxygen toxicity (e.g., bronchopulmonary dysplasia of the newborn and adult respiratory distress syndrome), reperfusion injury (e.g., following ischemia associated with myocardial infarction, open heart surgery, organ transplantation and shock), and inflammatory conditions and mitigating the effects thereof, for instance those involving the urinary tract and the joints, in various mammals. They are useful in alleviating the symptoms of and the structural deformities associated with post-traumatic arthritis, and rheumatoid diseases, such as bursitis, tendinitis, and osteoarthritis.

The invention is further illustrated by the following examples.

EXAMPLE 1

Fifty grams of PEG (a Union Carbide product labelled Polyox ® polyethylene oxide 100,000, equivalent to PEG 100,000 supplied by Aldrich Chemical Co., consisting of PEG partially isopropylated on one terminus, with a labeled molecular weight of 100,000 as determined by intrinsic viscosity measurement, and for which steric exclusion HPLC gave an average value of about 50,000) was dissolved in 1 liter of dry pyridine and 22 grams of succinic anhydride was added. The mixture was stirred for 38 hours at 60° C. The solvent was removed under vacuum at less than 60° C. and the residue was redissolved in 500 ml of water. The solution was washed with hexane and then the product was extracted into 1000 ml chloroform. The chloroform was removed under vacuum at 40° C. and the product was dissolved in benzene. The succinylated PEG was reprecipitated twice from benzene with petroleum ether.

Aqueous size exclusion HPLC using TSK PW 2500+4000 columns (Toyo Soda Manufacturing, Co., Ltd.) in series, calibrated with commercial PEG molecular weight standards, indicated that the average molecular weight of the PEG starting material was 50,000 and that the molecular weight of this PEG did not change after succinylation and purification by the procedure described above.

An aqueous solution of this succinylated PEG was size-fractionated to remove low molecular weight PEG by ultrafiltration using a Millipore ® Minitan ® apparatus equipped with a 300,000 (protein standard) nominal molecular weight limit membrane. The size-fractionated product was dried under vacuum. Analysis by aqueous size exclusion HPLC indicated that the average molecular weight of the succinylated PEG had increased from about 50,000 to about 80,000 as a result of ultrafiltration. The size-fractionated succinylated PEG thus obtained was then activated with N-hydroxysuccinimide. 12 gm of the succinylated PEG (molecular weight 80,000, 0.15 mmoles) was dissolved in 120 ml of dry dimethylformamide and 300 mg (2.6 mmoles) of N-hydroxysuccinimide was added, while stirring. After dissolution, 2.4 mmoles of dicyclohexylcarbodiimide was added and the solution was stirred at 40° C. for 30 minutes and then left unstirred at 24° C. for five days. The mixture was then filtered through a glass fiber filter and the filtrate was evaporated to dryness under vacuum at 40° C. The residue was dissolved with mild heating in 200 ml of dry toluene. The N-hydroxysuccinimidyl PEG was precipitated by addition of 400 ml of petroleum ether. The product was collected under vacuum on a glass fiber filter and then reprecipitated from toluene using petroleum ether, and then dried under vacuum. Size-exclusion HPLC showed that the molecular weight of the product had not changed as a result of activation.

A solution containing 80 mg of bovine Cu, Zn SOD (2.46 micromoles, 4400 Units/mg, from DDI Pharmaceuticals, Inc.) in 39 ml of 0.1M potassium phosphate buffer (pH 8.0) was added to 4 grams of the dry N-hydroxysuccinimidyl PEG derivative (50 micromoles) and the mixture was dissolved at 24° C. A solution of 80 mg human SOD can be substituted.

Size exclusion HPLC analysis showed that the coupling reaction was essentially complete within 1.5 hours, as was evident from the disappearance of unreacted SOD and appearance of a high molecular weight UV-absorbing adduct peak with a molecular weight of about 200,000.

The free PEG which had not coupled to SOD was separated from the PEG-SOD adduct by ion-exchange chromatography. Fractions containing PEG-SOD were collected by increasing the ionic strength of the elution buffer (pH 9) using NaCl. PEG-SOD fractions were dialyzed against water to remove buffer components and the concentrated by freeze-drying or vacuum evaporation.

As an example, the properties of a typical product eluted with 50 mM NaCl are described. The adduct contained 24 mg of SOD protein and 165 mg of protein-bound PEG. The protein content was determined by biuret analysis and the PEG content by HPLC, using refractive index detection (RI) and correcting for the RI contribution of the protein. The average molecular weight determined for the protein-bound PEG was 72,000. This MW for the PEG released from the adduct by proteolysis, combined with data showing that the ratio of SOD protein (32,000 MW) to PEG in the adduct was 24 mg to 165 mg, gives a ratio of 3 strands of PEG bound per molecule of SOD. The number of PEG strands per SOD molecule obtained in this way gives a calculated adduct MW of 220,000 (72,000 × 32,000/8), a result which is consistent with the MW obtained HPLC.

The SOD activity of the above adduct was determined using the cytochrome-C assay of McCord and Fridovich (J. Biol. Chem. 244: 6049–6055; (1969)). The specific activity of the PEG-SOD adduct (about 4317 units/mg proteine was 98% that of the native enzyme starting material (4400 units/mg). The product thus still retained almost all of the native enzymatic or biological activity, while satisfying other requirements of the invention.

The PEG-SOD derivative obtained as described in this Example was compared to the hightly purified, unmodified SOD starting material for immunologic sensitization potential (ability to cause anaphylactic reactions) in adult female Swiss Webster mice using a sensitization/challenge test. Ten mice were immunized by 4 subcutaneous injections during 2 weeks with 0.075 mg of protein per dose and then challenged intravenously with the same compound with 0.04 mg of protein at 21 day intervals thereafter. Whereas by the 5th intravenous challenge, in the group receiving unmodified SOD, 5 animals had died and 3 out of the 5 remaining animals shows signs of anaphylaxis, none of the 10 animals receiving the same dose of PEG-SOD showed any signs fo anaphylaxis.

When a PEG-SOD adduct containing approximately 6 strands of methoxy-PEG 5,000 per molecule of SOD was tested using the same protocol, by the fifth challenge, two out of 10 animals died and 4 of the remaining animals showed signs of anaphylaxis. Therefore, the PEG-SOD produced by the present invention, containing 3 strands of 72,000 MW PEG per SOD was less immunogenic than a PEG-SOD containing twice as many strands of 5,000 MW PEG.

EXAMPLE 2

Following the PEG-activation and coupling method of Example 1, PEGs of high molecular weight were prepared from PEG labeled 100,000 or 200,000 and were coupled to bovine Cu, Zn SOD. A PEG-SOD with 5 strands of 100,000 MW PEG and another with 3 strands of 120,000 MW PEG were each found to be less immunogenic in mice than native SOD or a product with 4 strands of 35,000 MW PEG.

EXAMPLE 3

The serum persistence of bovine native SOD was compared to that of PEG-SODs prepared by the method of Example 1 using adult female Swiss Webster mice. One PEG-SOD adduct tested contained 2 strands of about 65,000 MW PEG and another contained 4 strands of about 40,000 MW PEG. 100 micrograms of bovine SOD protein was injected intravenously. Blood was collected at regular intervals and the plasma was assayed for specific PEG-SOD activity by an electrophoretic method that separates PEG-SOD from mouse SOD. The half-life for the disappearance of native SOD in mice was 5–10 minutes, while the half-life for the disappearance of both of these PEG-SOD adducts was greater than 36 hours and PEG-SOD activity could be detected in the blood of these animals for at least 9 days. Another PEG-SOD preparation containing an average of 2.6 strands of PEG 45,000 MW also produced a half-life exceeding 36 hours; the PEG used to form this PEG-SOD was a molecular weight standard supplied by Toyo Soda Manufacturing Co., Ltd. It had a molecular weight of 45,000.

EXAMPLE 4

An aqueous solution of partially isopropylated PEG (Union Carbide) which was labelled as 100,000 MW (weight average determined by intrinsic viscosity), but with an average MW of about 50,000 measured by HPLC, was size-fractionated by ultrafiltration using a Millipore Minitan apparatus equipped with a 300,000 (protein standard) molecular weight cut-off membrane. The size-fractionated product was dried under vacuum. Analysis by HPLC showed that the average MW of the sample increased from 50,000 to 100,000 after ultrafiltration. To a solution containing 3.77 grams of such size-fractionated PEG in 100 ml of dry acetonitrile, 1.39 grams of cyanuric chloride in 2.8 ml of dry acetonitrile was added. After standing for 3 days at 24° C. the solution was diluted with an equal volume of acetonitrile and then clarified by filtration. The solvent was removed by evaporation under vacuum at 30° C. and the residue was redissolved in 120 ml of dry toluene. The product was precipitated by the addition of 360 ml of dry hexane. The product was reprecipitated once more from toluene using petroleum ether and dried under vacuum to yield cyanuric chloride-activated PEG. Size-exclusion HPLC demonstrated that the MW of the PEG did not change as a result of activation. Varying amounts of activated PEG, obtained as described above, were tested for ability to couple to bovine Cu, Zn SOD, present at a constant level of 1 mg/ml. The final PEG concentrations ranged from 5 to 100 mg/ml. After reacting for 24 hours at 24° C., the mixtures were assayed by HPLC with UV detection for the formation of PEG-SOD and also for the amount of residual SOD.

TABLE 1

| PEG:SOD in Reaction | | Percent Conversion of SOD To Adduct | Adduct Peak MW* |
|---|---|---|---|
| (w:w) | (M:M) | | |
| 5 | 1.7 | 25% | — |
| 10 | 3.3 | 29% | 90K |
| 20 | 6.6 | 62% | 140K |
| 50 | 16.7 | 90% | 150K |
| 75 | 24.0 | 95% | 200K |
| 100 | 33.3 | 100% | 200K |

*Determined by HPLC on TSK PW columns calibrated with commercial PEG standards.

As shown in Table 1, at a 50:1 (w/w) PEG to SOD input ratio in the reaction mixture (16.7:1 molar ratio), 90% of the SOD was converted to PEG-SOD with an average molecular weight of 150,000. At greater PEG to SOD ratios in the reactions, both the amount of SOD converted to PEG-SOD and the molecular weight of the adduct increased. The resulting sizes of the adducts indicate that up to two strands of 100,000 MW PEG can be attached to SOD under these conditions using cyanuric acid as the coupling agent.

The serum persistence in mice was measured for the PEG-SOD products from the 10:1 (w:w) and 75:1 (w:w) PEG to SOD reactions listed in Table 1, containing an average of 1 and 2 strands of PEG per molecule, respectively. The same methods used in Example 3 above, were employed. Half-lives of at least 36 hours were obtained for both products tested.

EXAMPLE 5

Ten grams of partially isopropylated 100 kilodalton polyethylene glycol (labelled PEG 100,000; Union Carbide) were freeze-dried for 24 hours to remove any moisture present in the sample. The dried 100K PEG was dissolved in approximately 45 ml of dry acetonitrile. Then 5.12 grams of 1,1-carbonyldiimidazole was added and the reaction mixture was incubated at room temperature for 1.5 hours, and then quenched in deionized water to destroy the excess carbonyldiimidazole. The pH was maintained at 7 to prevent hydrolysis of the activated PEG. The mixture was then dialyzed for 1 day at 4° C. against 4 liters of distilled water using at least 10 changes to remove the acetonitrile and imidazole. After dialysis, the activated PEG was chromatographed on a Sephacryl S-400 column in deionized water in order to separate the activated 100K-PEG from low molecular weight fragments.

To the resulting activated PEG there was added enough bovine SOD to produce a molar ratio of 3 moles of PEG per mole of SOD. 92.8 mg SOD was added to the pool (vol. = 108 ml). The mixture was freeze-dried 4 times in order to produce the desired PEG—O—CO—SOD product.

EXAMPLE 6

To a solution of 30 grams of Union Carbide polyethylene glycol (labeled 100,000 MW Polyox, with HPLC molecular weight of 50,000) in 1100 ml of dry dioxane at 35° C., there was slowly added under nitrogen and with stirring 10 grams of sodium hydride. After an additional hour of stirring at 25° C., 15 ml ethyl bromoacetate was added. The solution was stirred at 25° C. for 30 minutes, then for two hours at 45° C. and the reaction was terminated by addition of 200 ml of water. 400 ml of petroleum ether were then added with stirring. The organic phase was discarded and the viscous, aqueous phase was washed with petroleum ether. The aqueous phase containing the PEG ethyl ester was diluted to approximately 1 L and saponified by raising the temperature to 60°-70° C. for five hours. Finally, the PEG carboxyl groups were converted to the free acid by acidification to pH 2. The remaining bromoacetic acid was removed by dialysis or gel filtration. The PEG ether thus prepared can be substituted for the succinylated PEG used in Example 1.

Thus, using 9.4 grams of activated polyethylene glycol of a molecular weight of 40,000 (activated by the method of this Example) and 7.9 mg of bovine SOD there was obtained an adduct containing an average of 3.3 strands of PEG per molecule of SOD. The molecular weight of the product, as determined by HPLC, was about 140,000. This adduct had greatly reduced immunogenicity in mice.

Using 6.5 grams of polyethylene glycol of a molecular weight of 120,000 (activated by the method of this Example after size fractionation) and 87 mg of bovine SOD, there was obtained an adduct with two PEG strands and a molecular weight of about 245,000 as determined by HPLC.

EXAMPLE 7

The use of the process of this invention was established with human SOD. 20 mg samples of activated, succinylated PEG were placed into glass tubes. 100 mcl. of a solution of 3 mg/ml human SOD in 0.2 molar pH 8 phosphate-borate buffer were added. After mixing, 2 mcl samples of each reaction mixture were removed and quenched in 58 mcl of 0.01M 1:1 sodium acetate:acetic acid buffer in 250 microliter microtubes. To monitor the progress of the reaction, samples were electrophoresed at pH 8.5 using 250 volts for 15 minutes followed by nitroblue tetrazolium staining for determination of SOD activity.

After 3-3.5 hours at room temperature, the solutions were quenched with 45 microliters of 0.03 molar 1:1 acetate buffer per mg PEG. Addition of 0.1 ml of pH 8 reaction buffer and 0.9 ml 30 mM acetate produced a final pH of 6.4. This pH drop and dilution stopped further PEG-SOD coupling and hydrolysis. It was found that there was no appreciable further reaction after 30-45 minutes.

While the human PEG-SOD with strands of 19,000 Dalton PEG, like free SOD, was no longer detectable in mouse serum one day after injection, the preparation with strands of 30,000 Dalton PEG gave a prolonged persistence time.

The following example demonstrates the principles of this invention using recombinant human SOD expressed in fungi (Allelix, Inc.). A series of coupling reactions was prepared by adding a solution of recombinant human SOD (4 mg/ml protein in 0.1M phosphate-borate buffer, pH 8.0) to succinylated, activated, Fluka Chemicals 41,000 Dalton PEG (based on steric exclusion HPLC using PEG MW standards) to give PEG to SOD weight ratios of 4:1, 8:1, 12:1 and 16:1. PEG succinylation and activation was accomplished by the methods described in Example 1. After 1.5 hours at 23° C., the coupling reactions were terminated by lowering the pH by 2-fold dilution in 0.2M sodium dihydrogen phosphate. The reaction products were assayed by steric exclusion HPLC and UV and refractive index detection of PEG-SOD and of unconjugated human SOD. The activity of the reaction products was confirmed by assay for SOD activity using the cytochrome-c assay of McCord and Fridovich (J. Biol. Chem. 244: 6049–6055, 1969). The results are shown in Table 2.

TABLE 2

| PEG:SOD in reaction | | % Conversion[a] of SOD to Conjugate | Conjugate MW Range[a] | Avg. No. Strands in Conjugate |
|---|---|---|---|---|
| (w:w) | (M:M) | | | |
| 4 | 3.1 | 76% | 53K–154K | 1.5 |
| 8 | 6.2 | 96% | 53K–154K | 3 |
| 12 | 9.4 | 100% | 100K–450K | 4.5 |
| 16 | 12.5 | 100% | 150K–600K | >5 |

[a]Determined by HPLC on Ultrahydrogel 250 + 500 columns calibrated with commercial PEG standards.

Thus, natural or recombinant human SOD can be substituted for bovine SOD used in the preceding Examples. Typically, conjugation is carried out with activated dihydroxy PEG or terminally monomethylated, monoethylated or monoisopropylated PEG with average molecular weight of 40,000, 45,000, 65,000, 75,000, 120,000 and 200,000 as determined by HPLC.

EXAMPLE 8

A mouse carrageenan-induced paw edema test was employed to estimate anti-inflammatory activity of bovine PEG-SOD. In the paw edema test 0.03 ml of 1.0% carrageenan in saline was injected subcutaneously into the right hind foot pads of female Swiss Webster mice and then, 30 minutes later, the animals were dosed subcutaneously with 100 microliters of test compound which was prepared by dilution in saline followed by filter sterilization. Twenty four hours after the carrageenan injection the animals were sacrificed and both hind feet amputated and weighed. Edema was calculated as weight of the injected foot (right) minus weight of uninjected foot (left). The average and standard deviation of the edema weight for each treatment group, including a saline control group, was calculated.

At a dose of 30 micrograms per mouse, a bovine PEG-SOD adduct with 2.6 strands of 45,000 MW PEG (from Example 3) was more effective in reducing the edema than an adduct with 3.4 strands of 21,000 MW PEG (43% inhibition versus 14% inhibition, respectively). The 21,000 MW PEG was a molecular weight standard from Toyo Soda Manufacturing Co., Ltd. An adduct with 3 strands of 120,000 MW PEG (from Example 2) demonstrated 41% edema inhibition at a dose of 10 micrograms per mouse. Native, bovine Cu/Zn SOD was inactive in this assay, even when tested at 300 micrograms per mouse, as was an adduct prepared with 14 strands of methoxy-PEG 5,000 when tested at 100 micrograms per mouse.

EXAMPLE 9

As an antigenicity assay, a solid-phase, competitive-binding enzyme immunoassay (ELISA) was used to measure the cross-reactivity of PEG-SOD compounds containing bovine Cu,Zn SOD with rabbit antibody directed against highly purified native bovine Cu,Zn SOD. Conjugates of this invention required fewer strands of PEG to reduce antigenicity than compounds prepared with shorter strands, e.g., with methoxy-PEG 5,000. For example, an adduct with an average of 2.6 strands of 45,000 MW PEG (from Example 3) and one with 4 strands of 35,000 MW PEG (from Example 2) were one-third and one-tenth as antigenic, respectively, as an adduct with 6 strands of methoxy-PEG 5,000. The adduct with 2.6 strands of 45,000 MW PEG was about one-half as antigenic as an adduct with 2.4 strands of 21,000 MW PEG. The adduct with 4 strands of 35,000 MW PEG was half as antigenic as the one containing 14 strands methoxy-PEG 5,000. Among adducts with less than 4 PEG strands, those with PEG in the 100,000–120,000 MW range were less antigenic than adducts with the same number of shorter strands. Thus, a SOD adduct with 2 PEG strands of MW 120,000 (from Example 6) was only one fifth as antigenic as one with 2 strands of 35,000 MW PEG.

What is claimed is:

1. A method of producing a prolonged superoxide dismutase effect in a mammal wherein there is administered to that mammal an amount effective for producing a superoxide dismutase effect of a water-soluble substantially non-immunogenic conjugate of a superoxide dismutase coupled with a coupling agent to 1 to 5 strands of a polyalkylene glycol which is a polyethylene glycol or polyethylene-polypropylene glycol copolymer residue, wherein the said polyalkylene glycol so coupled has an average molecular weight as determined by HPLC using PEG as standard of about 35,000–200,000 and is unsubstituted or substituted at one terminal by a $C_{1-4}$-alkyl group.

2. The method of claim 1, wherein the polyalkylene glycol is at least partially substituted at one terminal by a $C_{1-4}$-alkyl group.

3. The method of claim 1, wherein the polyalkylene glycol is a polyethylene glycol of average molecular weight of about 40,000–200,000 as determined by HPLC.

4. The method of claim 1, wherein the polyethylene glycol is a polyethylene glycol of average molecular weight of about 40,000–150,000.

5. The method of claim 1, wherein 2 to 4 polyethylene glycol groups are coupled to each copper- and zinc-containing superoxide dismutase molecule.

6. The method of claim 1, wherein 2 to 4 polyethylene glycol groups are coupled to each superoxide dismutase molecule.

7. The method of claim 1, wherein the polyalkylene glycol is a monoisopropoxypolyethylene glycol.

8. The method of claim 1, wherein a terminal group of a polyethylene glycol is attached through a CO link to terminal amino groups of superoxide dismutase lysines.

9. The method of claim 1, wherein the superoxide dismutase coupled has substantially the structure of a human-derived superoxide dismutase.

10. The method according to claim 1, of providing prolonged relief from oxygen toxicity to a mammal in need thereof, wherein there is administered a sterile injectable aqueous solution of the water-soluble substantially non-immunogenic conjugate.

* * * * *